US00PP15891P3

(12) United States Plant Patent

Ramming et al.

(10) Patent No.: US PP15,891 P3

(45) Date of Patent: Jul. 26, 2005

(54) GRAPEVINE PLANT DENOMINATED 'SWEET SCARLET'

(50) Latin Name: *Vitis vinifera L.*
Varietal Denomination: Sweet Scarlet

(75) Inventors: David W. Ramming, Fresno, CA (US); Ronald E. Tarailo, Fresno, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 170 days.

(21) Appl. No.: 10/371,512

(22) Filed: Feb. 20, 2003

(65) Prior Publication Data

US 2004/0168236 P1 Aug. 26, 2004

(51) Int. Cl.[7] ..... A01H 5/00
(52) U.S. Cl. ..... Plt./205
(58) Field of Search ..... Plt./205

(56) References Cited

PUBLICATIONS

Ramming, D. et al., "An Update on the USDA Table Grape Breeding Program," *Dinuba Table Grape Seminar—1993 Proceedings*, Oral Presentation.

Ramming, D., "*USDA Grape Breeding Program and Promising Experimental Selections*," San Joaquin Valley Table Grape Seminar, Feb. 21, 2001 Visalia, CA.

Ramming, D. et al., "Development of Seedless Grapes for the Fresh Market Including Types Resistant to Powdery Mildew—2001," *Viticulture Research Report, California Table Grape Commission* (2002) vol. XXX.

Ramming, D. et al., "Development of Seedless Grapes for the Fresh Market Including Types Resistant to Powdery Mildew," *Viticulture Research Report, California Table Grape Commission* (2001) vol. XXIX.

Ramming, D. et al., "Development of Seedless Grapes for the Fresh Market—1999," *Viticulture Research Report, California Table Grape Commission* (2000) vol. XXVIII.

Ramming, D. et al., "Development of Seedless Grapes for the Fresh Market—1998," *Viticulture Research Report, California Table Grape Commission* (1999) vol. XXVII.

Ramming, D. et al., "Development of Seedless Grapes for the Fresh Market—1997," *1997–1998 Research Report, California Table Grape Commission* (1998) vol. XXVI.

Ramming, D. et al., "Development of Seedless Grapes for the Fresh Market—1996," *1996–1997 Research Report for California Table Grapes*(1997) vol. XXV.

Ramming, D. et al., "Development of Seedless Grapes for the Fresh Market—1995," *1995–1996 Research Report for California Table Grapes* (1996) vol. XXIV.

Ramming, D. et al., "Development of Seedless Grapes for the Fresh Market—1994," *1994–1995 Research Report for California Table Grapes*(1995) vol. XXIII.

Ramming, D. et al., "Development of Seedless Grapes for the Fresh Market—1993," *1993–1994 Research Report for California Table Grapes* (1994) vol. XXII.

Ramming, D. et al., "Development of Seedless Grapes for the Fresh Market—1992," *1992–1993 Research Report for California Table Grapes* (1993) vol. XXI.

United States Dept. of Agriculture Research Agreement—Memorandum of Understanding Agreement No. 58–5302–3–476 (1993).

*Primary Examiner*—Kent Bell
(74) *Attorney, Agent, or Firm*—Margaret A. Connor; John D. Fado; Lesley Shaw

(57) ABSTRACT

A new and distinct variety of grapevine denominated 'Sweet Scarlet' which is characterized by its midseason ripening seedless fruit, attractive raspberry red coloration, its ovoid fruit shape, its firm fruit texture with a light muscat flavor, and its medium to tight cluster.

2 Drawing Sheets

STATEMENT REGARDING FEDERALLY SPONSORED RESEARCH OR DEVELOPMENT

The new variety was developed by the United States Department of Agriculture of the Agricultural Research Service, Postharvest Quality and Genetics Research Unit in Parlier, Calif.

Latin name of the genus and species of the plant claimed: *Vitis vinifera* L.

Variety denominated: 'Sweet Scarlet'.

BACKGROUND OF THE INVENTION

The present invention relates to a new and distinct variety of grapevine, *Vitis vinifera* L., which will hereinafter be denominated varietally as the 'Sweet Scarlet' grapevine, and, more particularly, to a grapevine which has fruit maturing for commercial harvesting and shipment approximately August 23 in the San Joaquin Valley of central California. The fruit has an attractive red skin coloration at maturity with a muscat flavored flesh and outstanding fruit quality.

The grapevine of the present invention originated from a hand-pollinated cross of United States Department of Agriculture selection 'C33-30' (unpatented) and the United States Department of Agriculture selection 'C103-141' (unpatented) made in 1989 at the United States Department of Agriculture, Agricultural Research Service, Postharvest Quality and Genetics Research Unit plots at California State University, Fresno, in Fresno Calif. The female was 'C33-30' a seedless, red-fruited grapevine having reflex anthers in the flower, large oval berries with firm flesh and medium skin, and a neutral flavor. The fruit of the 'C33-30' ripen about one week before the instant variety. The pollen parent was 'C103-141' a seedless red-purple fruited grape with medium size, oval to round berries with medium skin and firm flesh. The fruit of the 'C103-141' grapevine ripen at the same time as the variety of the subject invention. Both of the parents of the instant cultivar are hybrids of the grapevine genus and species *Vitis vinifera* L.

Aborted seeds resulting from this controlled hybridization were developed further through invitro tissue culture and germinated in the laboratory during the fall of 1989. The resulting seedlings were planted in the spring of 1990 in a vineyard at the United States Department of Agriculture, Agricultural Research Service plots on the California State University, Fresno, campus in Fresno, Calif. The seedlings fruited in the summer of 1992 and one, the grapevine of the present invention, was selected for its attractive red seedless firm muscat flavored fruit, medium berry size, and outstanding fruit quality.

In 1993 at the inventors' direction, the grapevine of the subject invention was propagated asexually by rooting hardwood cuttings at Fresno, Calif. and a test planting of five grapevines of the subject invention was established in the United States Department of Agriculture, Agricultural Research Service plots on the California State University, Fresno campus. Subsequently, larger test plantings have been established with asexually multiplied grapevines of the instant invention. When hardwood cuttings were used for propagation, the instant cultivar rooted readily therefrom. All grapevines of the new variety planted from hardwood cutting propagation, fruited in the third season of growth after planting. All propagules, or resulting plants, of the present invention have been observed by the inventors to be true to type in that all asexual reproduced grapevines of the variety possessed the characteristics identical to those of the originally discovered grapevine.

SUMMARY OF THE INVENTION

The grapevines of the subject invention possess medium vigor and have produced fruit well both as own-rooted and grafted grapevines. The size of the grapevines was determined by growing the grapevines on a three cross arm 'T' type trellis structure with a top cross arm of 122 cm in length set 189 cm above the ground; a second cross arm of 102 cm in length set 156 cm above the ground; and a third cross arm 91 cm in length set 125 cm above the ground. The trellis structure had two wires per cross arm and indicted a grapevine height of 216 cm and a grapevine spread of 218 cm.

The fruit of the new variety ripens in midseason, about the same time as the 'Ruby Seedless' grapevine (unpatented). The average ripening date in Fresno, Calif. is August 23. Berries adhere well to the fruit pedicel and have minimal shatter from the clusters during storage. The fruit is raspberry red in color at maturity. The fruit shape is ovoid. Fruit skins are medium thick and similar to the 'Ruby Seedless' grapevine. 'Sweet Scarlet' differs from 'Ruby Seedless' by having a light muscat flavor. The pulp of the fruit adheres to the skins of the berry and the fruit texture is firm and meaty. The berries are medium in size, or 3.6 grams. The flavor of the fruit is sweet and has a light muscat flavor when ripe. The flavor has been rated high. Soluble solids concentration of the juice at fruit maturity averages 21.6% with titratable acid of 0.47 grams/100 milliliters of juice. The fruit is of the stenospermocarpic type of seedlessness and contains small, aborted seed traces that are not noticeable when eaten. The fruit clusters are usually borne on the average of 0.53 per shoot on cane pruned vines. The fruit clusters are conical and are large in size, or 1681 grams, medium to slightly tight and attractive. The fruit cluster peduncles are medium in length.

The grapevine and fruit of the new variety are susceptible to powdery mildew disease of grape plants. A spray program for powdery mildew disease control is required.

BRIEF DESCRIPTION OF THE DRAWINGS

The drawings of the grapevine of the present invention are color photographs showing in FIG. 1 a typical specimen of the fruit and in FIG. 2 a shoot with leaves and a flower cluster all of the new variety of the present invention. The color of the photographs is as nearly true as it is reasonably possible to provide in such color photographs. Description of the new invention applies to vines of 'Sweet Scarlet' grown on its own roots at a density of 1,119 vines per hectare in Fresno County, Calif. in 2002. These vines were in their fourth year of full production having been planted in 1996.

DETAILED BOTANICAL DESCRIPTION

Figure 1:
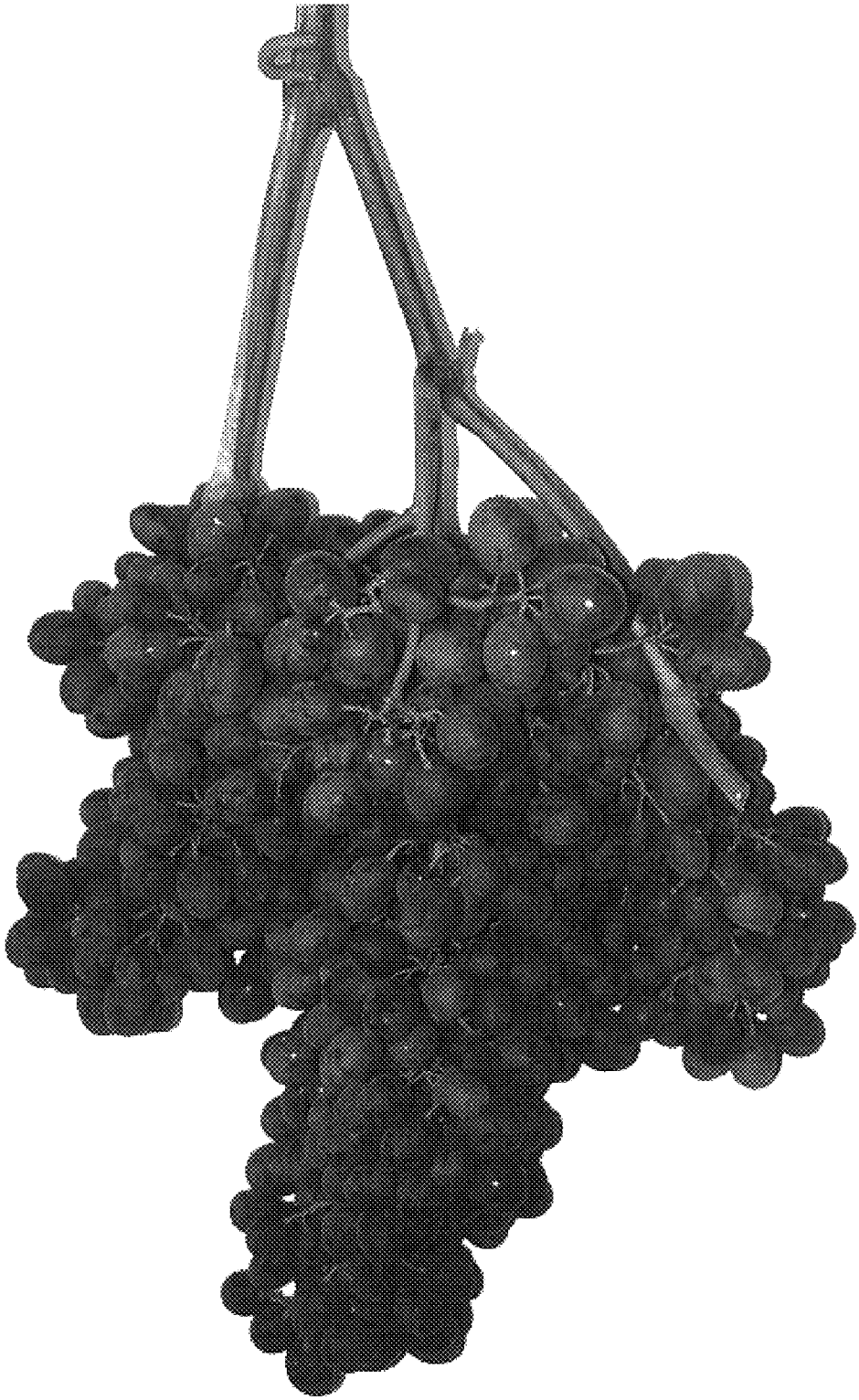
Figure 2:
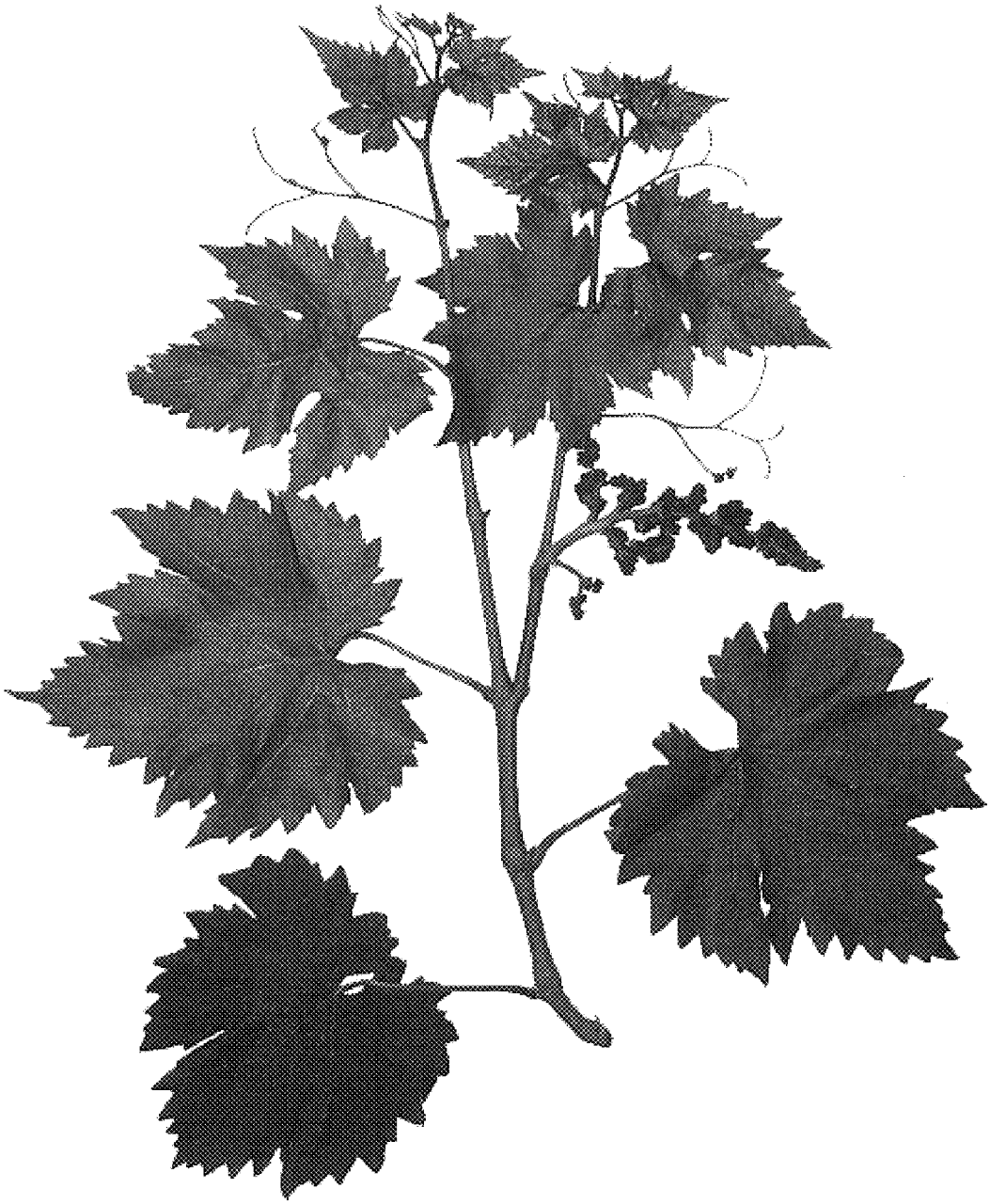

The new variety cv. 'Sweet Scarlet' may be distinguished from other commercial grape cultivars known to us by a combination of characteristics, including its midseason ripening seedless fruit with attractive raspberry red coloration, its firm fruit texture with a light muscat flavor, its ovoid fruit shape and its medium to tight cluster.

The new variety of grapevine is most similar to its pollen parent 'C103-141' by having similar dates of harvest and similar berry size. It is distinguished therefrom and an improvement thereon in a number of fruit characteristics. The flesh of the new variety is firmer, the skin color is an attractive raspberry red not a purple red coloration. The berry shape is ovoid compared to the oval to round berries of 'C103-141'. The most distinguishing difference is the light muscat flavor that is not present in the pollen parent. The new grapevine is also similar to the commercial variety 'Ruby Seedless' (unpatented) in that they ripen at a similar time, both have large clusters and similar size and shape berries. It is distinguished therefrom and an improvement thereon in that the flesh of the new variety is firmer, the color is more attractive being a raspberry red compared to a dull purple red of 'Ruby Seedless'. The most distinguishing difference is the light muscat flavor of the new variety.

The new variety also differs substantially from its mother parent 'C33-30'. The new variety has perfect flowers with functional male and female parts while 'C33-30' has only functional female parts. The new variety has smaller aborted seeds. The most distinguishing difference is the light muscat flavor of the new variety, while 'C33-30' has none.

Referring more specifically to the botanical details of this new and distinct variety of grapevine, the following has been observed under the ecological conditions prevailing at the orchard of origin which is located in Fresno in the San Joaquin Valley of central California. All major color code designations are by reference to the *Dictionary of Color,* by Maerz and Paul, First Edition, 1930. Common color names are also occasionally employed. Where dimensions, sizes, colors and other characteristics are given, it is to be understood that such characteristics are approximations of averages set forth as accurately as practicable. The description hereof was taken from specimens grown in Fresno, Calif. The grapevines used for measurement were grown in a fine sandy loam soil and the grapevines were irrigated using trickle, or drip irrigation. In a substantial part, the data hereof was from grapevines that were six (6) years old.

VINE

Generally:

*Size.*—Medium. Grapevine size as determined on grapevines growing on a three cross arm 'T' trellis with the top cross arm 122 cm (47.58 inches) long set 189 cm (73.71 inches) above the ground; the second cross arm 102 cm (39.78 inches) long set 156 cm (60.84 inches) above the ground; and the third cross arm 91 cm (35.49 inches) long set 125 cm (48.75 inches) above the ground. There were two wires per cross arm and was trained to produce a grapevine height of 216 cm (84.24 inches) and a grapevine spread of 218 cm (85.02 inches).

*Vigor.*—Medium vigor. Vigor as measured by weighing prunings at dormant pruning for cane pruned grapevines (with 5 canes and an average of 13 buds per cane) was 3.0 Kg.

*Productivity.*—Productive, 15.89 Kg per grapevine as compared to the Ruby Seedless grapevine which produces 16.8 Kg per grapevine on grapevines spaced 8 ft. (243.84 cm) by 12 ft. (365.76 cm).

*Regularity of bearing.*—Regular. Annual pruning of canes is required for reliable production.

CANES

Size:

*Diameter — mature canes.*—Medium diameter, medium vigor, upright in growth habit.

Mature canes:

*Diameter — internode base.*—11.4 mm (0.456 inches).

*Diameter — internode midpoint.*—9.1 mm (0.364 inches).

*Diameter — internode tip.*—5.4 mm (0.216 inches).

*Diameter — node base.*—12.7 mm (0.508 inches).

*Diameter — node midpoint.*—10.5 mm (0.42 inches).

*Diameter — node tip.*—7.5 mm (0.3 inches).

Internode length:

*Base.*—10.0 cm (3.9 inches).

*Midpoint.*—10.1 cm (3.939 inches).

*Tip.*—9.1 cm (3.549 inches).

*Average length of canes.*—240.8 cm (93.912 inches).

*Surface texture.*—Smooth.

*Color of mature cane.*—Brown (plate 11 H6). No anthocyanin observed on mature canes.

Buds:

*Color.*—Brown (plate 13 F8).

*Texture.*—Smooth.

Dormant bud (compound bud or eye):

*Width.*—At base of cane 5.3 mm (0.212 inches); at midpoint of cane 5.4 mm (0.216 inches) and at tip of cane 4.4 mm (0.176 inches). The average number of buds on a current, single-season growth cane is 26.

*Date of bud break.*—March 3$^{rd}$, midseason.

*Young shoots.*—Young shoots have cobwebby indument.

*Diameter of young shoots in spring (measured when shoots are 24 inches).*—At base 8.5 mm (0.34 inches), at midpoint 7.4 mm (0.296 inches) and at tip 3.1 mm (0.124 inches).

*Internode length.*—11.2 cm (4.368 inches) at 4$^{th}$ internode from base.

Young shoots:

*Color.*—Pale yellow green (plate 18 L7) with slight copper on edge.

Stem of shoot tip:

*Color.*—Green (plate 20 L6) with a slight copper tint in sun.

Shoot:

*Shape.*—Straight to slightly curved.

Shoot tip:

*Form.*—Open.

Tendrils:

*Size.*—Length — 25.2 cm (9.828 inches).

*Size.*—Diameter — 2.45 mm (0.098 inches).

*Shape.*—Usually triforcated or quadforcated and curled on distal end.

*Pattern.*—Found beginning opposite node 6 and 7, then again at nodes 9, 10, 12, 13, 15, 16 with this repeating intermittent pattern to the distal end of the cane.

Tendril:

*Color immature growth.*—Yellow green (plate 21 L6) with slight copper on tip.

Disease resistance: Susceptible to powdery mildew, and fungicides were applied to the grapevines under evaluation to control powdery mildew.

Insect resistance: Insecticides were applied to the grapevines under evaluation to control grapevine leafhoppers and variegated leafhoppers. No resistances to these pests were determined in these evaluations due to chemical control of these pests.

LEAVES

Size:

*Generally.*—Leaves simple and alternate. The mid vein (L1) is 14.9 cm (5.811 inches) long, vein L2 is 12.2 cm (4.758 inches) long and vein L3 is 8.9 cm (3.471 inches) long. The angle between the mid vein L1 and L3 is 55.1 degrees and between L1 and the 1st vein off L3 is 148.8 degrees.

*Average length.*—20.6 cm (8.034 inches).

*Average width.*—18.9 cm (7.371 inches).

*Shape.*—Orbicular.

Lobes:

*Number.*—Five (5).

Color:

*Upwardly disposed surface.*—Dark green (plate 23 H9). Upward surface is glabrous, flat and smooth to slightly bullate.

*Downwardly disposed surface.*—Green (plate 22 I6). Lower surface is glabrous with short hairs along the main midrib vein.

*Leaf vein.*—Light green (plate 19 I6) with occasional red (plate 6 I4) on main veins near center of leaf.

*Leaf vein — thickness.*—Thickness of mid vein at center of leaf is 1.9 mm (0.076 inches).

*Leaf margin.*—Serrated with shape of teeth pointed and medium in size.

*Petiole sinus.*—Lyre shape and usually petiole lobes overlap causing a closed petiole sinus. On mature leaf is 4.4 cm (1.72 inches) deep and 1.3 cm (0.507 inches) wide at widest point.

Anthocyanin:

*Main veins — location.*—With occasional red (plate 6 I4) on main veins near center of leaf.

Petiole:

*Size.*—Medium.

*Length.*—11.7 cm (4.563 inches).

*Diameter.*—3.3 mm (0.132 inches).

*Color.*—Green (plate 20 L4) with occasional red (plate 6 I4) covering.

Color:
*Young leaf — upper surface.*—Pale green (plate 21 L8) with light copper and cobwebby indument on upper surface.
*Young leaf — lower surface.*—Pale green (plate 22 K7).
*Shape unfolded — young leaf.*—Concave to flat.
*Petiole of young leaf — color.*—Medium green (plate 21 L8).
*Stipules.*—Onion skin.

TRUNK

Size: Large.
*Height.*—Approximately 104 cm (40.56 inches) above the vineyard floor.
*Diameter.*—7.41 cm (2.8899 inches) as measured just below the cordon or head point at 81.28 cm (31.6992 inches) above vineyard floor; and 6.81 cm (2.6559 inches) at 15.2 cm (5.928 inches) above the vineyard floor.
*Bark — color.*—(plate 16 A2).

FLOWERS

Flower:
*Size — generally.*—Medium.
*Unopened — diameter.*—2.8 mm (0.112 inches).
*Unopened — length.*—2.2 mm (0.088 inches).
*Unopened — surface texture.*—Smooth.
*Date of bloom.*—First bloom May 10.
*Date of full bloom.*—May 14 at 90%.
*Inflorescence.*—Panicle.
Cluster size:
*At bloom.*—Generally, large to very large.
*Cluster — length.*—27.3 cm (10.647 inches).
*Width.*—24.6 cm (9.594 inches).
Peduncle:
*Length.*—3.3 cm (1.287 inches).
*Shape of cluster.*—Conical with shoulder well developed.
Calyptra:
*Color.*—Green (plate 20 L6).
*Stamens.*—Five (5) and erect.
*Pistil.*—Well developed.
Ovary:
*Color.*—Green (plate 20 L8).
*Pollen.*—Normal, fertile, abundant.
Anthers:
*Color.*—Straw (plate 10 G2).

FRUIT

Maturity when descried: Ripe for commercial harvesting and shipment approximately August 23 in Fresno, Calif. Midseason or with the 'Ruby Seedless' grapevine.
Cluster:
*Size — cane pruned vines.*—1,681 grams (58.835 oz).
*Length.*—31.0 cm (12.09 inches).
*Width.*—23.0 cm (8.97 inches).
*Shape.*—Conical.
*Density.*—Medium to tight, on average has 460 berries per cluster.
*Clusters per vine.*—25.
*Clusters per shoot.*—0.53 clusters per shoot.
Peduncle:
Size:
*Length.*—Medium, 5.0 cm (1.95 inches).
*Diameter.*—Medium, 6.3 mm (0.252 inches).
*Color.*—Green (plate 20 K6).
*Texture.*—Smooth, glabrous.
Pedicel:
*Generally.*—There is a medium to good attachment between the berry and the pedicel.
*Size — length.*—7.4 mm (0.296 inches).
*Size — diameter.* —0.95 mm (0.038 inches).
*Color.*—Green (plate 20 H7).
*Texture.*—Glabrous with a few lenticels.
Brush:
*Length.*— 2.6 mm (0.104 inches).
*Brush color.*—Green (plate 20 D2).
Berry:
*Size.*—Medium, avg. 3.6 grams (0.126 oz).
*Shape.*—Ovoid 2.07 cm (0.8073 inches) long and 1.70 cm (0.663 inches) wide.
*Length.*—2.07 cm (0.8073 inches).
*Width.*—1.70 cm (0.663 inches).
*Color.*—Raspberry red (plate 6 I15).
*Bloom.*—Light.
Skin:
*Generally.*—The skin adheres to the flesh.
*Thickness.*—Medium in thickness.
*Texture.*—Smooth.
*Tendency to crack.*—None.
Flesh:
*Flesh color.*—Translucent and very pale yellow green (plate 18 B1).
*Texture.*—Firm, meaty.
*Juice production.*—Medium.
*Color of juice.*—Clear.
*Flavor.*—Sweet and sub acid, light muscat flavor.
*Soluble solids.*—21.6%.
*Titratable acid.*—0.47 g/100 ml juice.
*Aroma.*—None.
*Ripening.*—Uniform.
*Eating quality.*—Very good, sweet.
Character of seeds: Stenospermocarpic seedless, small aborted seed traces that are not noticeable when eaten. Average aborted seed trace when present are 11.5 mg fresh weight, 4.85 mm (0.194 inches) long and 2.51 mm (0.1004 inches) wide. Seed color is auburn (plate 7 C11).
Use: Fresh market. No wine nor raisin evaluations have been done.
Keeping quality: Good.
Resistance to disease: No resistance to powdery mildew.
Shipping and handling qualities: Berries ship and handle similar to 'Ruby Seedless' except the pedicel dries somewhat quicker.

Although the new variety of grapevine possesses the described characteristics noted above as a result of the growing conditions prevailing in Fresno, Calif. in the central San Joaquin Valley of California, United States of America, it is to be understood that variations of the usual magnitude and characteristics incident to changes in growing conditions, training, irrigation, fertilization, pruning, pest control, climatic variation and the like are to be expected.

Having thus described and illustrated our new variety of grapevine, what we claim as new and desire to be secured by Plant Letters Patent is:

1. A new and distinct variety of grapevine plant, 'Sweet Scarlet', substantially as illustrated and described, characterized by its attractive raspberry red fruit color, ovoid fruit shape, and firm flesh texture with a light muscat flavor.

* * * * *